United States Patent
Schuessler

(10) Patent No.: US 6,602,452 B2
(45) Date of Patent: Aug. 5, 2003

(54) ROTATIONAL MOLDING OF MEDICAL ARTICLES

(75) Inventor: David J. Schuessler, Ventura, CA (US)

(73) Assignee: McGhan Medical Corporation, Santa Barbara, CA (US)

( * ) Notice: Subject to any disclaimer, the term of this patent is extended or adjusted under 35 U.S.C. 154(b) by 158 days.

(21) Appl. No.: 09/908,414

(22) Filed: Jul. 18, 2001

(65) Prior Publication Data

US 2003/0018387 A1 Jan. 23, 2003

(51) Int. Cl.[7] .............................................. B29C 41/06
(52) U.S. Cl. ...................... 264/102; 264/139; 264/219; 264/225; 264/226; 264/227; 264/255; 264/310; 264/311
(58) Field of Search ................................. 264/301, 302, 264/304, 310, 311, 219, 220, 225, 226, 338, 102, 139, 255

(56) References Cited

U.S. PATENT DOCUMENTS

| 3,439,079 A |   | 4/1969  | McDowell |
|-------------|---|---------|----------|
| 3,652,368 A | * | 3/1972  | Formo ........................ 425/256 |
| 3,788,382 A |   | 1/1974  | Daniel et al. |
| 4,157,931 A |   | 6/1979  | Bricot et al. |
| 4,394,340 A |   | 7/1983  | Tarumi et al. |
| 4,416,841 A |   | 11/1983 | Corea et al. |
| 4,548,779 A | * | 10/1985 | Steinberg et al. ........... 264/255 |
| 4,796,686 A |   | 1/1989  | Gayso |
| 4,836,963 A |   | 6/1989  | Gilman, Jr. |
| 4,865,787 A |   | 9/1989  | Vallance et al. |
| 4,882,107 A | * | 11/1989 | Cavender et al. ............. 264/51 |
| 5,096,627 A |   | 3/1992  | Vogelgesang et al. |
| 5,346,660 A | * | 9/1994  | Matsumoto .................. 264/69 |
| 5,356,589 A | * | 10/1994 | Sugalski ..................... 264/265 |
| 5,376,117 A |   | 12/1994 | Pinchuk et al. |
| 5,525,284 A | * | 6/1996  | Grimmer .................... 264/301 |
| 5,705,110 A | * | 1/1998  | Weber ......................... 264/83 |
| 5,738,812 A | * | 4/1998  | Wild .......................... 264/102 |
| 6,030,557 A | * | 2/2000  | Payne ........................ 264/40.5 |
| 6,180,203 B1| * | 1/2001  | Unkles ........................ 428/71 |
| 6,214,272 B1| * | 4/2001  | Gruenwald et al. ......... 264/255 |
| 6,409,954 B1| * | 6/2002  | Mulligan .................... 264/255 |

OTHER PUBLICATIONS

"Computer Controlled Liquid Rotational Moulding of Medical Prostheses", by S.H. Teoh, K.K. Sin, L.S. Chan, & C.C. Hang; Rotation Fall 1994.

* cited by examiner

Primary Examiner—Stefan Staicovici
(74) Attorney, Agent, or Firm—Milbank, Tweed, Hadley & McCloy LLP

(57) ABSTRACT

A system and method for molding the shell of a medical device or other molded article is provided. The system includes a multi-axis rotational molding machine in which a mold is mounted. The mold has a cavity in the shape of the article to be molded. The mold seals to hold a vacuum. In operation, silicone or other molding material is inserted into the mold, vacuum is applied to the mold, the mold is rotated about at least two axes and a molding material coats the inside walls of the mold to form the shell or other desired article. A rotationally molded medical article is also provided.

14 Claims, 3 Drawing Sheets

ROTATIONAL MOLDING OF MEDICAL ARTICLES

BACKGROUND OF THE INVENTION

This invention relates to producing castings of silicone elastomers from solvent-based silicone dispersions using a hollow mold and multi-axis rotation until the material devolatilizes to a non-flowable state and is cured.

Rotational molding of many industrial, consumer, and medical related parts from a variety of plastics is commonplace. The plastic materials are typically polyolefins in pellet or powder form, but some are flowable liquids, such as plastisols, with sufficiently low viscosity, i.e. less than 5000 cps.

The rotational molding or casting method and system of the present invention has utility in the manufacture of breast implants and other medical devices and articles having a thin-walled shell, typically formed from silicone elastomer, such as tissue expanders and low-pressure elastomeric balloons. Low-pressure elastomeric balloons are used, for example, in catheter fixation, occlusion of blood flow, bracytherapy, and as intraaortic or intragastric balloons for cardiovascular or ear-nose-and-throat procedures. Other articles include feeding tubes, enema cuffs, catheters, condoms, shunts, and embolic protection devices. The traditional method of manufacturing these articles is by dipping a mandrel in a solvent-based silicone dispersion to cast and form the shell.

SUMMARY OF THE INVENTION

A system and method for molding the shell of a medical device or other molded article is disclosed. The system includes a multi-axis rotational molding machine in which a mold is mounted. The mold has a cavity in the shape of the article to be molded. The mold seals to hold a vacuum.

In operation, silicone or other molding material is inserted into the mold, vacuum is applied to the mold, the mold is rotated about at least two axes and a molding material coats the inside walls of the mold to form the shell or other desired article.

A rotationally molded medical article is also disclosed.

DETAILED DESCRIPTION

Figure 1:
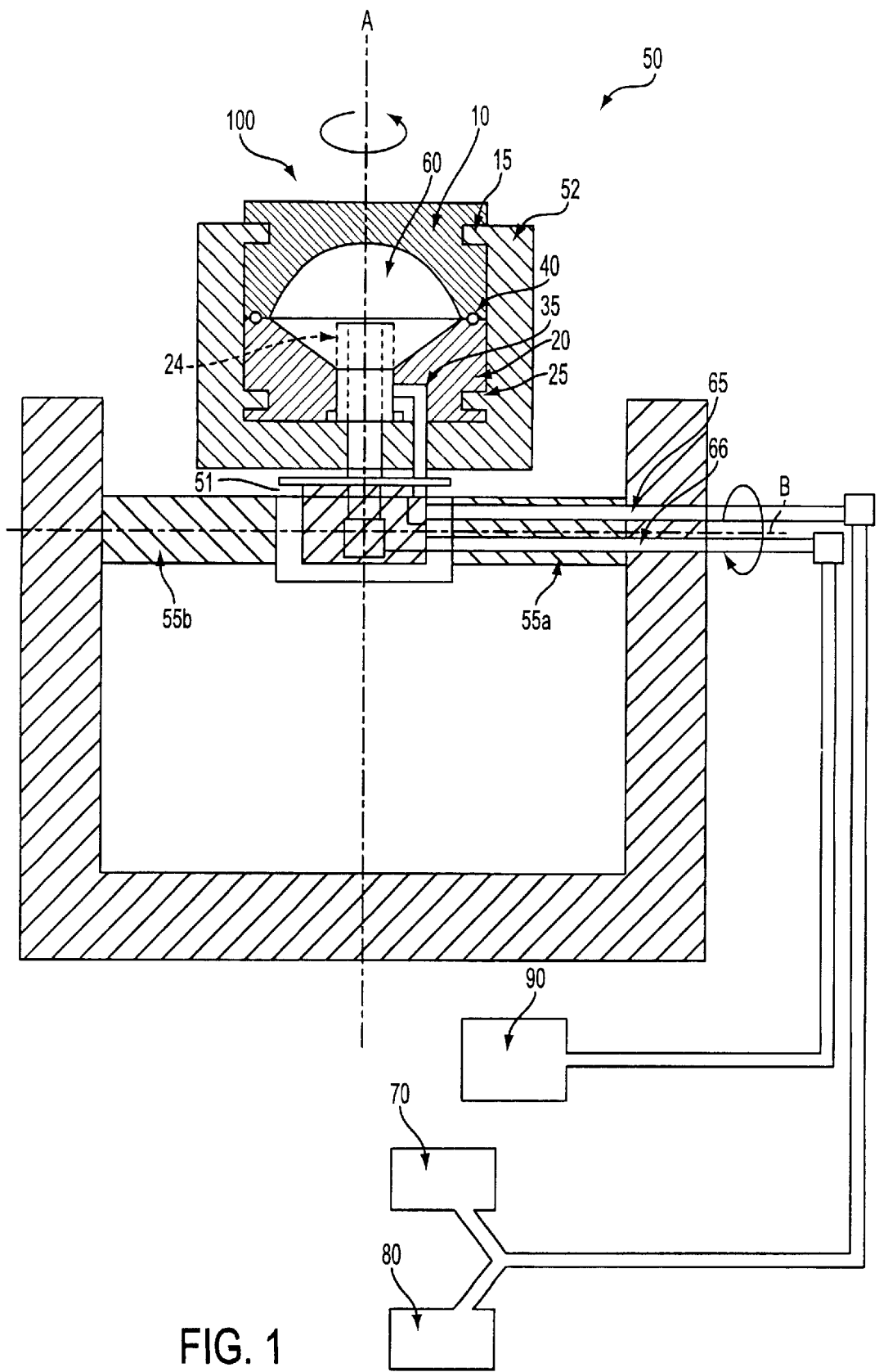
FIG. 1 is a schematic illustration of an embodiment of the rotational molding system of the present invention.
Figure 2:
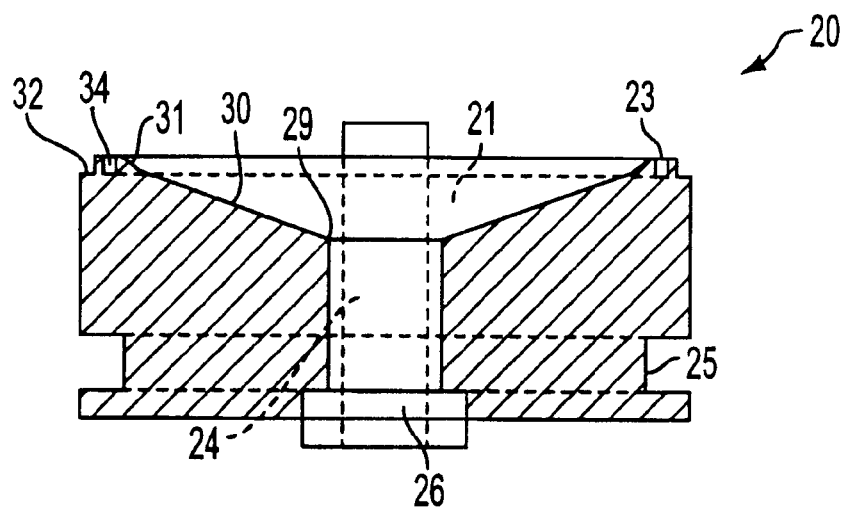
FIG. 2 is a cross-sectional schematic illustration of an embodiment of the bottom piece of the two-piece case mold.
Figure 3:
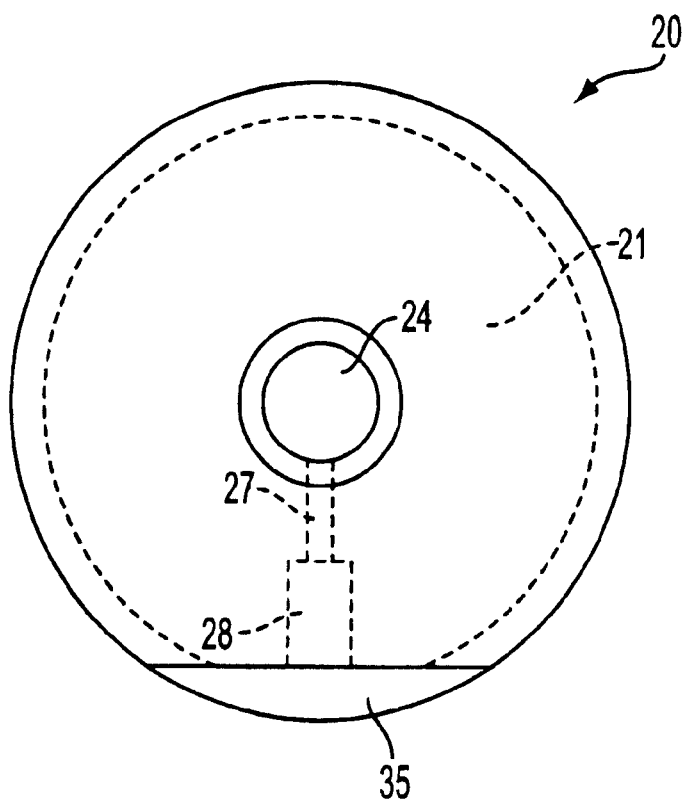
FIG. 3 is a top view schematic illustration of an embodiment of the bottom piece of the two-piece case mold.
Figure 4:
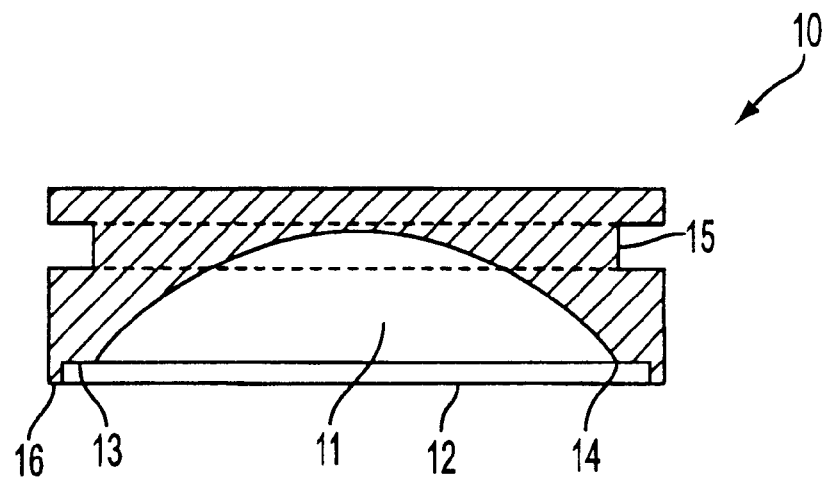
FIG. 4 is a cross-sectional schematic illustration of an embodiment of the top piece of the two-piece case mold.
Figure 5:
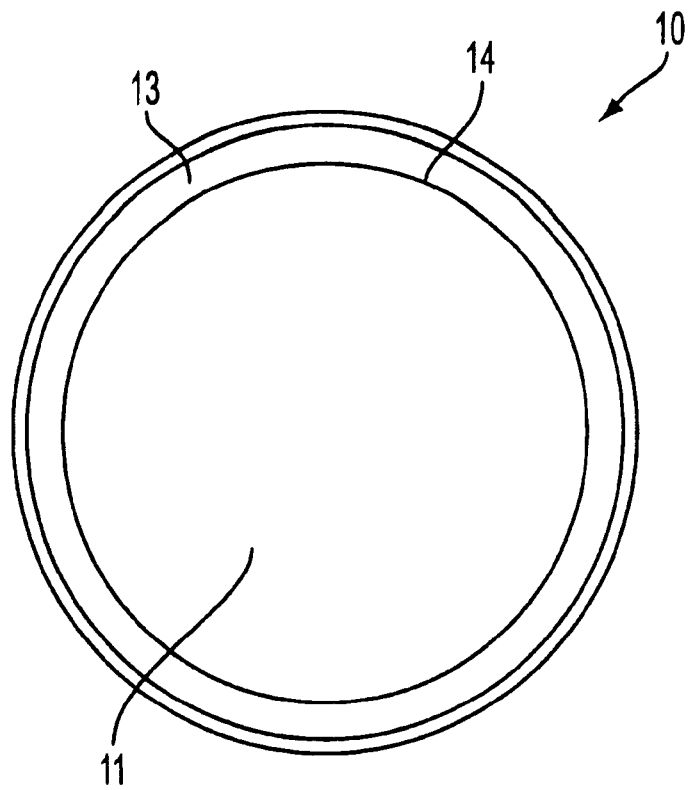
FIG. 5 is a top view schematic illustration of an embodiment of the top piece of the two-piece case mold.

The present invention relates to four novel developments using a rotational casting process that have direct application for improving the process and products for these existing medical devices.

The first development achieved by the rotational molding system and process of the present invention relates to its use in the rotational molding of silicones and other solvent-based or gas-emitting materials. This has not been feasible heretofore with most silicone elastomers, even LSR's (Liquid Silicone Rubbers), because silicone elastomers with sufficient physical properties for use with medical devices are usually high in molecular weight or require fillers. These materials typically have too high of a viscosity to be free-flowing as is required in a rotational molding process. Such higher molecular weight polymers need to be combined with a solvent to make a dispersion having a suitable viscosity. This solvent-based, reduced viscosity dispersion allows application of the silicone polymer onto a mandrel by spraying or dipping after which the solvent is allowed to evaporate. Such a solvent-based dispersion has not been practical for use in a rotational molding process since there is no ready means to remove the significant volume of solvent vapors that are trapped within the closed molds heretofore used in rotational molding processes. However, by adding a vacuum vent to the mold, e.g., one internal to the rotating arm of the equipment, a means is provided to remove the solvent while the arm is rotating and the dispersion material is flowing and being deposited on the inner surface of the mold. Alternatively the mold may be constructed of porous material, such as a porous metal or ceramic through which the solvent can be evacuated over the whole surface of the mold. This development of utilizing a vacuum vent or porous mold in a rotational molding process is applicable not only to silicones, but to any other materials which are solvent-based or emit gaseous by-products during curing such as polyurethanes or other polymers and the like.

A second aspect of the rotational molding system and process of the present invention relates to providing a means for molding seamless articles. Most articles made by rotational molding are made using multi-part hollow molds. It is often undesirable for medical products intended for implantation to have a seam or other surface irregularities. Even with precision machining of the mold, the articles produced by conventional rotational molding processes have, at a minimum, a witness parting line in their outer surface due to the mating surfaces of the mold. These mold parting lines are eliminated in the process disclosed in the present invention by first coating the inside of the assembled, multi-part mold with a thin layer of molding material such as polyethylene, polypropylene, polyester resin or the like to create a mold liner. After the liner is cast, then the raw material, e.g. silicone, polyurethane, or other polymer, for the desired article is injected into the mold cavity and similarly rotationally cast inside the liner resulting in a laminated construct. When the mold is disassembled and the construct is removed from the mold, the liner material and the desired article are physically separated resulting in the desired article having a seamless configuration.

A third aspect of the rotational molding system and process of the present invention relates to the ability to extract the desired article from a reusable, seamless, one-piece mold. Such a one-piece mold may be made from rotationally molded plastic or from a metal through an electrolytic nickel process, aluminum casting, "lost wax" technique or the like. Using any of these mold-making methods, a one-piece mold may be constructed having a very small opening, e.g. approximately 1" (2.54 cm) in diameter. Into this opening is placed a sprue for dispensing the raw material to be used in molding the desired article and a vacuum port. Because most medical devices made using the molding system and process of the present invention typically have very thin walls, e.g. from about 0.005" (0.0127 cm) to about 0.060" (0.1524 cm), the desired rotationally molded shell may be collapsed after it is cured by applying a vacuum to the inside of the article and/or by injecting air between the article and the wall of the one-piece mold. The thin-walled collapsed shell may then be extracted from the one-piece mold through the opening as the sprue is removed. This technique results in the desired molded article having an opening corresponding in size to the opening of the one-piece mold, which may then be patched or otherwise utilized in much the same way as the opening on articles produced using a mandrel.

A fourth development achieved by the rotational molding system and process of the present invention relates to its ability to produce a patchless molded article or shell. The primary component of any of the above-referenced medical devices is the shell. The current dipping technology to manufacture the shell used in these medical devices produces a shell hole because the shell must be cut open so that it can be removed from the mandrel on which it was formed. Subsequent steps in the construction of these medical devices involve patching the shell hole with a separate piece of silicone or the like. This patching process would not be necessary if the shell is formed under selected rotational molding methods as the shell would be whole and not require any cutting.

Besides the four novel developments described above, there are many other potential benefits and extensions of the rotational molding concept that one familiar with current manufacturing of shells and other medical articles can appreciate. The process could be modified to produce multi-layer, multi-material laminated shells. Surface texturing of the shell or other molded article is another possibility.

One benefit of the invention is its reduction in the overall use of solvent which allows for solvent condensation and recycling, as well as reducing and almost eliminating employee exposure to solvents used in the molding process. Another possible application is to fill the shell or other molded article with a filler such as a gel and cure the combined shell and filler while still in the mold for precise implant shaping. Soft solid fills and foamed structures such as NuSil MED4210 elastomer or Applied Silicone #50003 liquid foam are examples of these fill materials. Another interesting aspect is that due to the use of a liner, the mold surface never needs finishing. Silicone material waste is essentially eliminated compared to a dipping process. Less clean room space is required. The process is more automated, so should be more repeatable and easier to validate and support. The product produced is more uniform in thickness thereby enhancing the performance and quality of the final product. By reducing solvent use, the invention is environmentally friendly and generates less waste to be disposed.

Each embodiment of the present invention requires a source of multi-axis rotation in which a mold may be mounted. An example of such a multi-axis rotational mold machine is the Compact Clamshell sold by FSP Machinery. This two-axis rotational mold machine allows for an inert gas to be injected into the mold and controlled throughout the rotational cycle.

FIG. 1 is a schematic of an embodiment of the rotational molding system of the present invention. A two-piece case mold 100 is fixed to a multi-axis rotational mold machine 50 by clamps securing top mold piece 10 and bottom mold piece 20 to clamp base 52 at top locking groove 15 and bottom locking groove 25 respectively. Vacuum connection 65 runs through one arm of the mold machine 50 to the vacuum opening 35. Additionally, material connection tube 66, through which silicone or other molding material(s), polyethylene, polypropylene, nylon, fluoropolymer, polyester resin, polyurethane, epoxy or other liner materials, and/or air are injected into the mold cavity 60, may run through or along the same arm 55a as the vacuum connection 65 or by means of the other arm 55b. The hub 51 of the two arms rotates about axis A in the horizontal direction, while the arms 55 rotate about axis B, which maybe perpendicular to axis A. This allows the liner material and silicone material to uniformly coat the surface of the mold cavity 60. Two-piece case mold 100 may be manufactured from copper, aluminum, or other materials. The top mold piece 10 and bottom mold piece 20 are fitted together at their mating surfaces, sealed with O-ring 40, and then locked into clamp base 52 of multi-axis rotational molding machine 50. Material reservoir 90 is fluidly coupled to connection tube 66 for providing silicone or other molding material, liner material and/or air to cavity 60. Vacuum source 80 and solvent condenser 70 are fluidly coupled to vacuum connection 65.

A preferred embodiment of a two-piece case mold 100 of the present invention is illustrated in FIGS. 2–5. The interior of the top mold piece 10 defines a circular cavity which is used to form the top portion of the shell or molded article. In cross-section, top dome cavity 11 may be hemispherical in shape. At the edge 14 of the top dome cavity 11, near the bottom of the top mold piece 10, there is a top mold mating surface 13. Top mold mating surface 13 joins bottom mold mating surface 23 to form the parting line of the two-piece case mold 100. Along the outside edge of the top mold mating surface 13, located radially outward from the center of the top mold 10, is a lip 16 having a rectangular cross-section. Lip 16 runs around the circumference of the bottom edge of the top mold piece 10. The mold will seal to hold a vacuum along the parting line where the mating surfaces 13, 23 meet when the top mold piece 10 and the bottom mold piece 20 are engaged to form the two-piece case mold 100. Top locking groove 15, rectangular in cross-section, runs around the entire exterior of top mold piece 10 allowing top mold piece 10 to be fixed into clamp base 52 of the multi-axis rotational molding machine 50 during the molding process.

Bottom mold piece 20 may be composed of the same material as top mold piece 10 and may be constructed of copper, aluminum or other materials. Bottom mold piece 20 may be bigger than the top mold piece 10. Bottom mold piece 20 may have the same exterior dimensions or circumference as the exterior dimensions or circumference of top mold piece 10. However, the internal dimensions or circumference of bottom mold piece 20 and top mold piece 10 should coincide. Bottom mold piece 20 has a bottom locking groove 25, rectangular in cross-section, running around the entire exterior of bottom mold piece 20 allowing bottom mold piece 20 to be fixed into clamp base 52 of the multi-axis rotational molding machine 50 during the molding process. The interior of the bottom mold piece 20 defines a circular cavity 21 which is used to form the bottom portion of the shell or molded article. Bottom cavity 21 of bottom mold piece 20 may be hemispherical in cross-section similar to top dome cavity 11 but is more preferably defined by a shallow conical wall 30 sloping down to a circular opening 29. The circular opening 29 is connected to a circular sprue tube 24 having an outside diameter equal to the diameter of circular opening 29. Circular sprue tube 24 is coaxial with circular opening 29 of bottom mold piece 20 and connects to sprue opening 26 which is also circular. Sprue opening 26 allows for materials to enter into the two-piece case mold 100 when the bottom mold piece 20 and the top mold piece 10 are mated.

Also connected to the circular sprue tube 24 is an inner vacuum tube 27 perpendicular to the circular sprue tube 24.

Inner vacuum tube 27 is connected to outer vacuum tube 28 having a diameter greater than that of inner vacuum tube 27. Outer vacuum tube 28 is connected to vacuum opening 35 which in turn is connected to vacuum connection 65. The larger outer vacuum tube 28 allows the vacuum connection 65 to attach to the two-piece case mold and not enter the circular sprue tube 24.

Bottom mold mating surface 23 is different than the top mold mating surface 13 of top mold piece 10. As seen in the cross-section of FIG. 2, the outer edge of conical wall surface 30 transitions upward in a curve to form arc 31 such that when top mold piece 10 and bottom mold piece 20 are engaged at their respective mating surfaces, the edge of arc 31 is aligned with edge 14 of the mating surface 13 of top mold piece 10. Arc 31 allows the mold 100 to have a smooth transition surface from top mold piece 10 to the bottom mold piece 20 and further allows for the top mold piece 10 and the bottom mold piece 20 to form a tight seal when a vacuum is applied to the mold. Radially spaced away from the center of the bottom mold piece 20 and outside the perimeter of arc 31, O-ring groove 34 runs around the circumference of the top edge of the mating surface 23 of bottom mold piece 20. A typical elastomeric O-ring 40, e.g. a Viton® O-ring, is inserted into the O-ring groove 34 to maintain the integrity of the seal between top mold piece 10 and bottom mold piece 20. A locking ledge 32 is formed around the outside edge of bottom mold piece 20 into which a corresponding lip 16 of top mold piece 10 fits to maintain the orientation of the two mold pieces 10, 20 and form a seal when they are mated together and locked into the clamp base 52 of the multi-axis rotational molding machine 50 using locking grooves 15, 25. When top mold piece 10 and bottom mold piece 20 are mated together, the two-piece case mold 100 formed thereby defines the inside cavity 60 of the mold.

The first step in manufacturing a shell or other article utilizing the multi-axis rotational molding system of the present invention is to make a liner which coats the internal mold surface of the two-piece case mold 100. The liner should cover the interior surfaces of top dome cavity 11 and the bottom cavity 21. Covering the internal mold surface thus masks any interruptions in the surface, such as the mold parting lines, machining marks located on the internal mold surface, or minor damage to the internal mold surface. The liner may be any suitable material but should meet several requirements. First, the liner should have a low extractability level so it is biocompatible with the implant shell or other molded article. The liner should also be resistant to any solvent or solvents being used in the silicone or other materials used in making the implant shell or other molded article. The liner material should be able to completely and uniformly coat the internal mold surface during the rotation of the mold by the multi-axis rotational molding machine. If heat is used to cure the silicone during the molding process, the liner should have a high level of heat resistance. The liner should be easily removable or releaseable from the mold surface and from the cured shell or other molded article. Lastly, the liner may be used to impart a desired surface finish to the silicone elastomer or other material, e.g. glossy, matte, textured, etc. Suitable liner materials include: polyethylene (Equistar™ # MP658–662), polypropylene (A. Schulman™ #PD 8020), nylon (Capron® #8280); fluoropolymers (DuPont® Teflon® PFA), polyester resin (Hypol™ # 320300-10), polyurethane (Smooth-On Smooth Cast #305) and epoxy (Polytek® Development Corp. Polypoxy® 1010), all of which can be found on the open market. A skilled artisan in the field will recognize that other similar materials can replace these listed liner materials.

A predetermined volume or weight of the chosen liner material is dispensed into the mold so as to produce a lining of the desired thickness. The liner material is either in the form of a fine powder or a liquid depending on the selection of the liner material as long as the selected material is free flowing. The liner material is inserted into the two-piece case mold 100 through sprue opening 26 and circular sprue tube 24. Circular sprue tube 24 extends approximately halfway into the interior cavity 60 of case mold 100 and remains in this position during the entire process of forming a liner and shell or other article. The liner material can be inserted into the case mold prior to the case mold being locked into the rotational arms of the multi-axis rotational molding machine or after the case mold has been locked into the rotational arms. The closed mold 100 is rotated about two or more axes allowing the liner material inside to form a consistent coating along the internal surface of cavity 60. The rotation of the mold about the axes forms a liner of uniform thickness. If the liner material is composed of thermoplastics, heat is applied so as to cause the liner material to melt and coat the inside mold surface as per conventional rotational molding techniques. In the case a chemical set is used for the liner material system, such as a polyester resin, no heat needs to be applied. In addition, air pressure, vacuum, inert gas such as nitrogen or other vapors or solid particles may be applied to the interior of the mold to minimize bubbles or to affect the surface finish of the liner in the desired manner.

Once the liner has been formed, the next step is to form the shell or other desired article. Circular sprue tube 24 remains in the sprue opening 26 during the entire process of curing the liner and the molding material. To keep the sprue tube 24 clean and to maintain a vacuum during the casting step, the exterior end of the sprue has a removable cap. Silicone or other molding material is injected into the interior of the mold. A predetermined amount of molding material is inserted based on the desired size and thickness of the finished shell or article. For breast implants, the desired materials are usually silicones dispersed in a solvent. NuSil MED10-6605 is a good selection for a room temperature acetoxy-curing (RTV) silicone dispersion. NuSil MED 10-6400 may be used as platinum catalyzed heat-cured (HTV) silicone dispersion. Tin catalyzed silicones or polyurethanes may also be used, as well as other silicone elastomers or solvent systems.

After the silicone or other molding material has been dispensed into the mold cavity 60 with the liner via the sprue tube 24 and sprue opening 26, the mold is rotated around at least two axes while a vacuum is applied to its interior. The vacuum may be applied in different fashions. The vacuum can be applied to the sprue of a sealed mold by way of the vacuum opening 35. The vacuum may also be applied to the interior cavity or chamber in which an open sprue mold is rotating. Alternatively, the mold may be constructed of a porous material and a vacuum applied to the exterior of such porous mold. In addition, positive pressure using either, or in combination, air, nitrogen, or other gases may be applied intermittently to aid in bubble removal within the silicone elastomer or other molding material. Bubbles need to be removed to allow for a uniform smooth surface of the liner, and ultimately the shell or other molded article. In the case of RTV silicones, which require the presence of some water molecules in the mold cavity to carry out the condensation reaction, the applied positive pressure gas could include water vapor.

The silicone or other molding material is rotated and allowed to cure as the arms of the rotational molding machine rotate around their axes, thereby forming the desired shape. Rotating the mold at a higher speed can compensate for a lower viscosity level of the inserted materials. Heat is applied if necessary or to accelerate the curing process. The silicone or other material "sets up" and stops flowing as it is rotated and cures in place along with the liner material. If a laminated part is desired, the above steps may be repeated. If additional wall thickness is desired for the shell or other molded article, the steps may also repeated.

After the cure cycle has been completed and the silicone or other molding material has been cured to the desired thickness, the mold is opened at the parting line, i.e. where the mating surfaces of the top mold piece and the bottom mold piece converge. The formed shell or article surrounded by the liner is removed from the mold. The shell or other molded article is separated from the liner by one of the following methods appropriate to the liner system: dissolving the liner in a suitable solvent; melting or burning the liner away from the more temperature resistant shell or molded article; tearing or breaking the liner away from the shell; or peeling the flexible formed shell away from the liner and removing it through the opening in the liner created by the sprue opening. The liner may be discarded, or if the liner has not been damaged or dissolved depending on the separation process of the liner from the shell or molded article, the liner may be reused in the process again.

The mold is cleaned, if necessary, of any particles that might have remained from the previous manufacturing of the liner and shell or other article. After cleaning, the mold is ready for the next cycle. If the previously used liner is in satisfactory condition, the liner can be reused in the next molding process with or without a two-piece case mold.

If the shell is being used for breast implants, the formed shell is ready for further assembly or processing consistent with the usual manner in creating a final breast implant product. For example, the implant shell may be filled with a filler material of silicone gel, saline solution or other biocompatible filler material well known to those of skill in the art.

It will be understood that the above-described embodiments are merely illustrative of the principles of the invention and that other arrangements may be devised by those skilled in the art without departing from the spirit and scope of the invention.

What is claimed is:

1. A method for molding a medical article comprising the steps of:

inserting a liner material into a cavity within a mold;

rotating said liner material in said mold about at least two axes to uniformly coat the interior of said mold cavity with said liner material;

inserting a molding material into said cavity;

rotating said molding material in said mold about at least two axes to coat the interior of said liner material within said mold cavity with said molding material; and separating said liner material from said molding material to form the medical article.

2. The method of claim 1 further comprising the step of:

applying a vacuum to said mold.

3. The method according to claim 2 wherein said liner material coats the interior of said mold cavity thereby masking any surface irregularities.

4. The method according to claim 2 wherein said liner material is a thermoplastic selected from the group consisting of polyethylene, polypropylene, nylon and fluoropolymer.

5. The method according to claim 2 wherein said liner material is a thermoset selected from the group consisting of polyester resin, polyurethane and epoxy.

6. The method according to claim 1 wherein said molding material is a room temperature acetoxy-cured silicone dispersion in a solvent.

7. The method according to claim 1 wherein said molding material is a platinum catalyzed heat-cured silicone dispersion in a solvent.

8. The method of claim 1 wherein said liner material is separated from said molding material by dissolving said liner material.

9. The method of claim 1 wherein said liner material is separated from said molding material by melting said liner material.

10. The method of claim 1 wherein said liner material is separated from said molding material by burning said liner material.

11. The method of claim 1 wherein said liner material is separated from said molding material by peeling said liner material from said molding material.

12. The method of claim 1 further comprising the step of removing the medical article from the mold through an opening in the mold left by a sprue.

13. The method of claim 1 further comprising the step of inserting a filler material into said mold cavity.

14. The method of claim 13 further comprising the step of curing said filler material.

* * * * *